US011246866B2

(12) United States Patent
Sever et al.

(10) Patent No.: US 11,246,866 B2
(45) Date of Patent: Feb. 15, 2022

(54) SOLID PHARMACEUTICAL COMPOSITIONS FOR TREATING HCV

(71) Applicant: AbbVie Inc., North Chicago, IL (US)

(72) Inventors: Nancy E. Sever, Northbrook, IL (US); Ulrich Westedt, Schriesheim (DE); Ute Lander, Dannenfels (DE); Katrin Schneider, Mannheim (DE); Benedikt Steitz, Kallstadt (DE); Thomas Mueller, Ludwigshafen (DE); Regina Reul, Mannheim (DE); Constanze Obermiller, Heidelberg (DE); Adivaraha Jayasankar, Naperville, IL (US); Michael Simon, Landau (DE); Yi Gao, Vernon Hills, IL (US); Harald Hach, Oberotterbach (DE); Samuel Kyeremateng, Mannheim (DE); Katharina Asmus, Neustadt a.d.W. (DE); Ping Tong, Potomoc, MD (US); Donghua Zhu, Vernon Hills, IL (US); Marius Naris, Downers Grove, IL (US); Colleen Garrett, Chicago, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 16/654,442

(22) Filed: Oct. 16, 2019

(65) Prior Publication Data

US 2020/0253968 A1 Aug. 13, 2020

Related U.S. Application Data

(63) Continuation of application No. 15/212,997, filed on Jul. 18, 2016, now abandoned, which is a continuation-in-part of application No. 15/192,211, filed on Jun. 24, 2016, now abandoned.

(60) Provisional application No. 62/295,309, filed on Feb. 15, 2016, provisional application No. 62/193,639, filed on Jul. 17, 2015, provisional application No. 62/186,154, filed on Jun. 29, 2015, provisional application No. 62/185,145, filed on Jun. 26, 2015.

(51) Int. Cl.
| | |
|---|---|
| *A61K 31/498* | (2006.01) |
| *A61K 9/28* | (2006.01) |
| *A61K 9/20* | (2006.01) |
| *A61K 31/454* | (2006.01) |
| *A61K 9/24* | (2006.01) |
| *A61K 9/14* | (2006.01) |
| *A61K 31/4985* | (2006.01) |

(52) U.S. Cl.
CPC .......... *A61K 31/498* (2013.01); *A61K 9/146* (2013.01); *A61K 9/209* (2013.01); *A61K 9/2027* (2013.01); *A61K 31/454* (2013.01); *A61K 31/4985* (2013.01)

(58) Field of Classification Search
CPC .............................. A61K 31/498; A61K 9/146
See application file for complete search history.

(56) References Cited

U.S. PATENT DOCUMENTS

| | | | |
|---|---|---|---|
| 3,466,159 | A | 9/1969 | Abe et al. |
| 3,492,386 | A | 1/1970 | Tsuneo et al. |
| 3,648,037 | A | 3/1972 | Walter, Jr. |
| 3,680,106 | A | 7/1972 | Thomas |
| 3,685,984 | A | 8/1972 | Gilbert et al. |
| 3,809,265 | A | 5/1974 | Krenke et al. |
| 3,853,176 | A | 12/1974 | Henrich |
| 3,937,150 | A | 2/1976 | Miericke et al. |
| 6,087,386 | A | 7/2000 | Chen et al. |
| 8,466,159 | B2 | 6/2013 | Bernstein et al. |
| 8,492,386 | B2 | 7/2013 | Bernstein et al. |
| 8,648,037 | B2 | 2/2014 | Or et al. |
| 8,680,106 | B2 | 3/2014 | Bernstein et al. |
| 8,685,984 | B2 | 4/2014 | Bernstein et al. |
| 8,686,026 | B2 | 4/2014 | Liepold et al. |
| 8,716,454 | B2 | 5/2014 | Kullmann et al. |
| 8,809,265 | B2 | 8/2014 | Bernstein et al. |
| 8,853,176 | B2 | 10/2014 | Bernstein et al. |
| 8,937,150 | B2 | 1/2015 | Degoey et al. |
| 9,220,748 | B2 | 12/2015 | Or et al. |
| 9,333,204 | B2 | 5/2016 | Miller et al. |
| 2011/0207699 | A1 | 8/2011 | Degoey et al. |
| 2012/0004196 | A1 | 1/2012 | Degoey et al. |

(Continued)

FOREIGN PATENT DOCUMENTS

| | | |
|---|---|---|
| WO | WO-2008021927 A2 | 2/2008 |
| WO | WO-2008144380 A1 | 11/2008 |

(Continued)

OTHER PUBLICATIONS

Composiciones Farmacéuticas Sólidas Para EL Tratamiento Del VHC, Servicio Nacional de Derechos Intelectuales, IEPI-2018-689, 9 pages.

(Continued)

*Primary Examiner* — Kyle A Purdy

(57) ABSTRACT

The present invention features solid pharmaceutical compositions comprising Compound 1 and Compound 2. In one embodiment, the solid pharmaceutical composition includes (1) a first layer which comprises 100 mg Compound 1, as well as a pharmaceutically acceptable hydrophilic polymer and a pharmaceutically acceptable surfactant, all of which are formulated in amorphous solid dispersion; and (2) a second layer which comprises 40 mg Compound 2, as well as a pharmaceutically acceptable hydrophilic polymer and a pharmaceutically acceptable surfactant, all of which are formulated in amorphous solid dispersion.

27 Claims, No Drawings

(56) References Cited

U.S. PATENT DOCUMENTS

| | | |
|---|---|---|
| 2012/0070416 A1 | 3/2012 | Or et al. |
| 2012/0220562 A1 | 8/2012 | Degoey et al. |
| 2012/0264780 A1 | 10/2012 | Kullmann et al. |
| 2013/0102026 A1 | 4/2013 | Borody |
| 2013/0102525 A1 | 4/2013 | Bernstein et al. |
| 2013/0102526 A1 | 4/2013 | Bernstein et al. |
| 2013/0102557 A1 | 4/2013 | Bernstein et al. |
| 2013/0102558 A1 | 4/2013 | Bernstein et al. |
| 2014/0024579 A1 | 1/2014 | Bernstein et al. |
| 2014/0057835 A1 | 2/2014 | Bernstein et al. |
| 2014/0080868 A1 | 3/2014 | Ng et al. |
| 2014/0080869 A1 | 3/2014 | Krishnan et al. |
| 2014/0107016 A1 | 4/2014 | Bernstein et al. |
| 2014/0107017 A1 | 4/2014 | Bernstein et al. |
| 2014/0274934 A1 | 9/2014 | Bernstein et al. |
| 2014/0275099 A1 | 9/2014 | Bernstein et al. |
| 2014/0323395 A1 | 10/2014 | Bernstein et al. |
| 2015/0004196 A1 | 1/2015 | Perricone |
| 2015/0024999 A1 | 1/2015 | Awni et al. |
| 2015/0119400 A1 | 4/2015 | Ng et al. |
| 2015/0196615 A1 | 7/2015 | Awni et al. |
| 2016/0199374 A1 | 7/2016 | Miller et al. |
| 2016/0317602 A9 | 11/2016 | Awni et al. |
| 2016/0317603 A9 | 11/2016 | Awni et al. |
| 2016/0375017 A1 | 12/2016 | Asmus et al. |
| 2016/0375087 A1 | 12/2016 | Sever et al. |

FOREIGN PATENT DOCUMENTS

| | | |
|---|---|---|
| WO | WO-2009064975 A1 | 5/2009 |
| WO | WO-2010030359 A2 | 3/2010 |
| WO | WO-2010111348 A1 | 9/2010 |
| WO | WO-2010132601 A1 | 11/2010 |
| WO | WO-2010144646 A2 | 12/2010 |
| WO | WO-2011054834 A1 | 5/2011 |
| WO | WO-2011091417 A1 | 7/2011 |
| WO | WO-2011112558 A2 | 9/2011 |
| WO | WO-2011156578 A1 | 12/2011 |
| WO | WO-2012040167 A1 | 3/2012 |
| WO | WO-2012051361 A1 | 4/2012 |
| WO | WO-2014047039 A1 | 3/2014 |
| WO | WO-2014047046 A1 | 3/2014 |
| WO | WO-2014120981 A1 | 8/2014 |
| WO | WO-2014152514 A1 | 9/2014 |
| WO | WO-2015061742 A2 | 4/2015 |
| WO | WO-2015153793 A1 | 10/2015 |
| WO | WO-2017015211 A | 1/2017 |

OTHER PUBLICATIONS

Co-pending U.S. Appl. No. 15/212,997, filed Jul. 18, 2016.
Einav S., et al., "The Hepatitis C Virus (HCV) Ns4b RNA Binding Inhibitor Clemizole is Highly Synergistic with HCV Protease Inhibitors," The Journal of Infectious Diseases, 2010, vol. 202 (1), pp. 65-74.
European Association for the Study of the Liver, "EASL Clinical Practice Guidelines: Management of Hepatitis C Virus Infection," Journal of Hepatology, 2011, vol. 55 (2), pp. 245-264.
Corresponding U.S. Appl. No. 14/210,858.
Corresponding U.S. Appl. No. 14/210,870.
Food-Effect Bioavailability and Fed Bioequivalence Studies, 2002, 12 pages.
Franciscus, HCSP Fact Sheet, [online] [Retreived on Jan. 7, 2015] Retreived from the internet:<URL: www.hcvadvocate.org>.
Gilead Sciences, Inc. et al. v. Abbott Laboratories, Inc et al. Case No. 13-2034, U.S. District Court for the District of Delaware. Order Construing the Terms of U.S. Patent Nos. 8466159 & 8492386. Dated Nov. 3, 2015.
Grünberger C., et al., "3-Drug Synergistic Interaction of Small Molecular Inhibitors of Hepatitis C Virus Replication," Journal of Infectious Diseases, Journal of Infectious Diseases, 2008, vol. 197, pp. 42-45.
International Search Report and Written Opinion for Application No. PCT/US2014/027556, dated Jul. 2, 2014, 10 pages.
International Search Report and Written Opinion for Application No. PCT/US2015/023923, dated May 15, 2015, 10 pages.
International Search Report and Written Opinion for Application No. PCT/US2015/023923, dated May 19, 2015, 10 pages.
International Search Report and Written Opinion for Application No. PCT/US2016/039266, dated Sep. 28, 2016, 9 pages.
International Search Report and Written Opinion for Application No. PCT/US2016/041334, dated Oct. 24, 2016, 9 pages.
International Search Report and Written Opinion for Application No. PCT/US2016/042806, dated Sep. 28, 2016, 9 pages.
International Search Report for Application No. PCT/US2014/027423, dated Jun. 4, 2014, 3 pages.
Koev G., et al., "Antiviral Interactions of an HCV Polymerase Inhibitor with an HCV Protease Inhibitor or Interferon in Vitro," Antiviral Research, 2007, vol. 73 (1), pp. 78-83.
Lawitz E., et al., "A Phase 2a Trial of 12-Week Interferon-Free Therapy with Two Direct-Acting Antivirals (ABT-450/r, ABT-072) and Ribavirin in IL28B C/C Patients with Chronic Hepatitis C Genotype 1," Journal of Hepatology, Jul. 2013, vol. 19 (1), pp. 18-23.
Lawitz E.J., et al., "Potent Antiviral Activities of the Direct-Acting Antivirals ABT-493 and ABT-530 with Three-Day Monotherapy for Hepatitis C Virus Genotype 1 Infection," Antimicrobial Agents and Chemotherapy, Dec. 28, 2015, vol. 60(3), pp. 1546-1555.
Legrand-Abravanel F., et al., "Hepatitis C Virus Genotype 5: Epidemiological Characteristics and Sensitivity to Combination Therapy with Interferon-Alpha Plus Ribavirin," The Journal of Infectious Diseases, 2004, vol. 189 (8), pp. 1397-1400.
Lin C.W. et al., "P0715 : Steady-State Pharmacokinetics and Safety of Coadministration of Pan-Genotypic, Direct Acting Protease Inhibitor, ABT-493 with Pan-Genotypic NS5A Inhibitor, ABT-530, in Healthy Adult Subjects," Journal Of Hepatology, 2015, vol. 62 (2), p. S592.
Lok A., et al., Combination Therapy With BMS-790052 and BMS-650032 Alone or With Pegylated Interferon and Ribavirin (pegIFN/RBV) Results in Undetectable HCV RNA Through 12 Weeks of Therapy in HCV Genotype 1 Null Responders, 61th Annual Meeting of the American Association for the Study of Liver Diseases Boston, MA, Oct. 30-Nov. 3, 2010. Retrieved from the Internet: URL: http://www.natap.org/2010/AASLD/AASLD_16.htm.
Lok Anna S., et al., "Combination Therapy with BMS-790052 and Bms-650032 alone or with PEGIFN/RBV Results in Undetectable HCV RNA Through 12 Weeks of Therapy in HCV Genotype 1 Null Responders," Hepatology, Wiley, USA, 2010, vol. 52 (4, Suppl 1), p. 877A.
<gwmw class="ginger-module-highlighter-mistake-type-1" id="gwmw-15530399089919217913486">Medicamento</gwmw>, Forma galénica, 28 pages. http://es.wikipedia.org/wiki/Forma_gal%C3%A9nica.
Prichard M.N., et al., "A Three-Dimensional Model to Analyze Drug-Drug Interactions," Antiviral Research, 1990, vol. 14 (4-5), pp. 181-206.
Proceso 89-AI-2000, Tribunal de Justicia de la Comunidad Andina, Oct. 12, 2001, 40 pages. http://intranet.comunidadandina.org/documentos/Gacetas/gace722.pdf.
Suñé JM., "Nuevas Aportaciones Galénicas a Las Formas de Administración," Formación Continuada, Para Farmacéuticos De Hospital, pp. 28-65. http ://www.ub.es/legmh/capitols/sunyenegre.pdf.
Tanabe Y., et al., "Synergistic Inhibition of Intracellular Hepatitis C Virus Replication by Combination of Ribavirin and Interferon-a," The Journal of Infectious Diseases, 2004, vol. 189 (7), pp. 1129-1139.
Walpole S.C., et al., "The Weight of Nations: An Estimation of Adult Human Biomass," BMC Public Health, 2012, vol. 12, p. 439.
Wyles D.L., et al., "Synergy of Small Molecular Inhibitors of Hepatitis C Virus Replication Directed at Multiple Viral Targets," Journal of Virology, 2007, vol. 81 (6), pp. 3005-3008.

SOLID PHARMACEUTICAL COMPOSITIONS FOR TREATING HCV

RELATED APPLICATIONS

This application is a continuation of U.S. patent application Ser. No. 15/212,997, filed Jul. 18, 2016, which is a continuation-in-part of U.S. patent application Ser. No. 15/192,211, filed Jun. 24, 2016. The contents of each application are incorporated herein by reference. This application also claims the benefit of U.S. Provisional Application Nos. 62/185,145, filed Jun. 26, 2015, 62/186,154, filed Jun. 29, 2015, 62/193,639, filed Jul. 17, 2015 and 62/295,309, filed Feb. 15, 2016. The contents of each application are incorporated herein by reference.

FIELD OF THE INVENTION

The present invention relates to solid pharmaceutical compositions comprising anti-HCV compounds and methods of using the same for treating HCV infection.

BACKGROUND OF THE INVENTION

The hepatitis C virus (HCV) is an RNA virus belonging to the Hepacivirus genus in the Flaviviridae family. The enveloped HCV virion contains a positive stranded RNA genome encoding all known virus-specific proteins in a single, uninterrupted, open reading frame. The open reading frame comprises approximately 9500 nucleotides and encodes a single large polyprotein of about 3000 amino acids. The polyprotein comprises a core protein, envelope proteins E1 and E2, a membrane bound protein p7, and the non-structural proteins NS2, NS3, NS4A, NS4B, NS5A and NS5B.

Chronic HCV infection is associated with progressive liver pathology, including cirrhosis and hepatocellular carcinoma. Chronic hepatitis C may be treated with peginterferon-alpha in combination with ribavirin. Substantial limitations to efficacy and tolerability remain as many users suffer from side effects, and viral elimination from the body is often incomplete. Therefore, there is a need for new drugs to treat HCV infection.

DETAILED DESCRIPTION

The present invention features solid pharmaceutical compositions useful for treating HCV. These solid pharmaceutical compositions comprise:

(Compound 1)

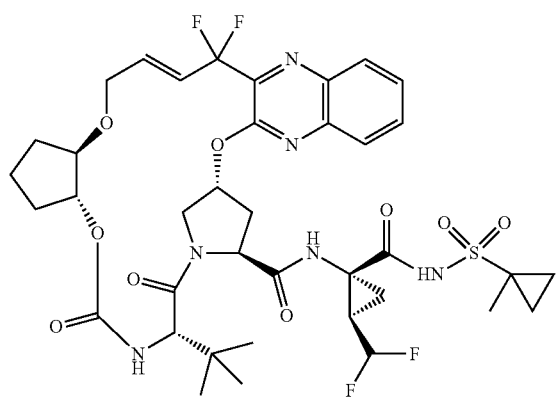

(1)

or a pharmaceutically acceptable salt thereof, formulated in amorphous solid dispersion, and (Compound 2)

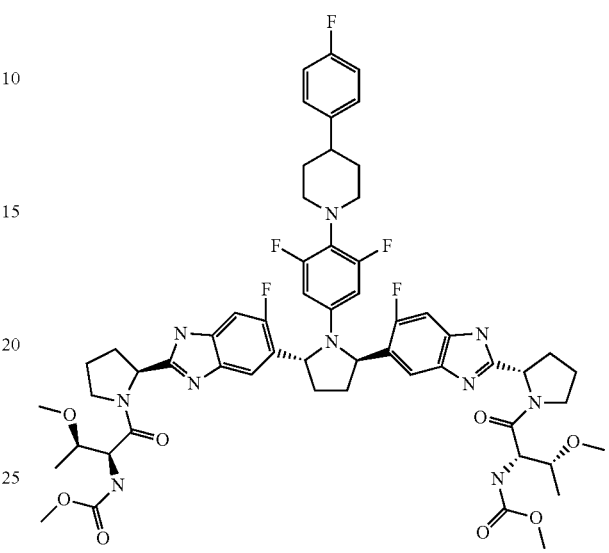

(2)

or a pharmaceutically acceptable salt thereof, formulated in amorphous solid dispersion.

Compound 1 is a potent HCV protease inhibitor and is described in U.S. Patent Application Publication No. 2012/0070416, which is incorporated herein by reference in its entirety. Compound 2 is a potent NS5A inhibitor and is described in U.S. Patent Application Publication No. 2012/0220562, which is incorporated herein by reference in its entirety.

In one embodiment, Compound 1 and Compound 2 are separately formulated in different amorphous solid dispersions. These solid dispersions are then milled and/or mixed with other excipients, to form a solid pharmaceutical composition that contains both Compound 1 and Compound 2.

In another embodiment, Compound 1 and Compound 2 are separately formulated in different amorphous solid dispersions. The solid dispersion comprising Compound 1 is milled and/or mixed with other excipients, and then compressed into a first layer of a tablet; and the solid dispersion comprising Compound 2 is likewise milled and/or mixed with other excipients, and compressed into a second layer of the same tablet.

In another embodiment, Compound 1 and Compound 2 are separately formulated in different amorphous solid dispersions. The solid dispersion comprising Compound 1 is milled and/or mixed with other excipients, and then compressed into mini-tablets, and each mini-tablet is no more than 5 mm in size. The solid dispersion comprising Compound 2 is likewise milled and/or mixed with other excipients, and compressed into mini-tablets, and each mini-tablet is no more than 5 mm in size. The mini-tablets containing Compound 1 are then mixed with the mini-tablets containing Compound 2, to provide the desired dosing for Compound 1 and Compound 2.

In another embodiment, Compound 1 and Compound 2 are separately formulated in different amorphous solid dispersions. The solid dispersion comprising Compound 1 is milled and/or mixed with other excipients, and then compressed into mini-tablets, and each mini-tablet is no more than 3 mm in size. The solid dispersion comprising Compound 2 is likewise milled and/or mixed with other excipients, and compressed into mini-tablets, and each mini-tablet is no more than 3 mm in size. The mini-tablets containing Compound 1 are then mixed with the mini-tablets containing Compound 2, to provide the desired dosing for Compound 1 and Compound 2.

In another embodiment, Compound 1 and Compound 2 are separately formulated in different amorphous solid dispersions. The solid dispersion comprising Compound 1 is milled and/or mixed with other excipients, and then compressed into mini-tablets, and each mini-tablet is no more than 2 mm in size. The solid dispersion comprising Compound 2 is likewise milled and/or mixed with other excipients, and compressed into mini-tablets, and each mini-tablet is no more than 2 mm in size. The mini-tablets containing Compound 1 are then mixed with the mini-tablets containing Compound 2, to provide the desired dosing for Compound 1 and Compound 2.

In yet another embodiment, Compound 1 and Compound 2 are formulated in the same amorphous solid dispersion. The solid dispersion is milled and/or mixed with other excipients, to provide a solid pharmaceutical dosage form that contains both Compound 1 and Compound 2.

In still another embodiment, Compound 1 and Compound 2 are formulated in the same amorphous solid dispersion. The solid dispersion is milled and/or mixed with other excipients, and then compressed into a tablet.

In a yet another embodiment, a solid pharmaceutical composition of the invention comprises:

(1) Compound 1 or a pharmaceutically acceptable salt thereof, formulated in a first amorphous solid dispersion, wherein the first amorphous solid dispersion further comprises a pharmaceutically acceptable hydrophilic polymer and a pharmaceutically acceptable surfactant; and (2) Compound 2 or a pharmaceutically acceptable salt thereof, formulated in a second amorphous solid dispersion, wherein the second amorphous solid dispersion further comprises a pharmaceutically acceptable hydrophilic polymer and a pharmaceutically acceptable surfactant.

In yet another embodiment, a solid pharmaceutical composition of the invention is a tablet which comprises:

(1) a first layer comprising a first amorphous solid dispersion, wherein the first amorphous solid dispersion comprises (i) Compound 1 or a pharmaceutically acceptable salt thereof, (ii) a pharmaceutically acceptable hydrophilic polymer and (iii) a pharmaceutically acceptable surfactant; and (2) a second layer comprising a second amorphous solid dispersion, wherein the second amorphous solid dispersion comprises (i) Compound 2 or a pharmaceutically acceptable salt thereof, (ii) a pharmaceutically acceptable hydrophilic polymer and (iii) a pharmaceutically acceptable surfactant.

In a yet another embodiment, a solid pharmaceutical composition of the invention comprises:

(1) 100 mg Compound 1 formulated in amorphous solid dispersion which further comprises a pharmaceutically acceptable hydrophilic polymer and a pharmaceutically acceptable surfactant; and (2) 40 mg Compound 2 formulated in amorphous solid dispersion which further comprises a pharmaceutically acceptable hydrophilic polymer and a pharmaceutically acceptable surfactant.

In a yet another embodiment, a solid pharmaceutical composition of the invention comprises:

(1) 100 mg Compound 1 formulated in amorphous solid dispersion which further comprises copovidone and Vitamin E polyethylene glycol succinate (Vitamin E TPGS); and (2) 40 mg Compound 2 formulated in amorphous solid dispersion which further comprises copovidone and Vitamin E TPGS.

In a yet another embodiment, a solid pharmaceutical composition of the invention comprises:

(1) 100 mg Compound 1 formulated in amorphous solid dispersion which further comprises copovidone and Vitamin E TPGS; and (2) 40 mg Compound 2 formulated in amorphous solid dispersion which further comprises copovidone, Vitamin E TPGS and propylene glycol monocaprylate.

In yet another embodiment, a solid pharmaceutical composition of the invention is a tablet which comprises:

(1) a first layer which comprises 100 mg Compound 1, as well as a pharmaceutically acceptable hydrophilic polymer and a pharmaceutically acceptable surfactant, all of which are formulated in amorphous solid dispersion; and (2) a second layer which comprises 40 mg Compound 2, as well as a pharmaceutically acceptable hydrophilic polymer and a pharmaceutically acceptable surfactant, all of which are formulated in amorphous solid dispersion.

In yet another embodiment, a solid pharmaceutical composition of the invention is a tablet which comprises:

(1) a first layer which comprises 100 mg Compound 1, as well as copovidone and Vitamin E TPGS, all of which are formulated in amorphous solid dispersion; and (2) a second layer which comprises 40 mg Compound 2, as well as copovidone and Vitamin E TPGS, all of which are formulated in amorphous solid dispersion.

In yet another embodiment, a solid pharmaceutical composition of the invention is a tablet which comprises:

(1) a first layer which comprises 100 mg Compound 1, as well as copovidone and Vitamin E TPGS, all of which are formulated in amorphous solid dispersion; and (2) a second layer which comprises 40 mg Compound 2, as well as copovidone, Vitamin E TPGS and propylene glycol monocaprylate, all of which are formulated in amorphous solid dispersion.

In a yet another embodiment, a solid pharmaceutical composition of the invention comprises:

(1) a first type of mini-tablets, each of which is no more than 5 mm in size and comprises an amorphous solid dispersion including (i) Compound 1 or a pharmaceutically acceptable salt thereof, (ii) a pharmaceutically acceptable hydrophilic polymer and (iii) a pharmaceutically acceptable surfactant; and (2) a second type of mini-tablets, each of which is no more than 5 mm in size and comprises an amorphous solid dispersion including (i) Compound 2 or a pharmaceutically acceptable salt thereof, (ii) a pharmaceutically acceptable hydrophilic polymer and (iii) a pharmaceutically acceptable surfactant.

In a yet another embodiment, a solid pharmaceutical composition of the invention comprises:

(1) a first type of mini-tablets, each of which is no more than 3 mm in size and comprises an amorphous solid dispersion including (i) Compound 1 or a pharmaceutically acceptable salt thereof, (ii) a pharmaceutically acceptable hydrophilic polymer and (iii) a pharmaceutically acceptable surfactant; and (2) a second type of mini-tablets, each of which is no more than 3 mm in size and comprises an amorphous solid dispersion including (i) Compound 2 or a pharmaceutically acceptable salt thereof, (ii) a pharmaceutically acceptable hydrophilic polymer and (iii) a pharmaceutically acceptable surfactant.

In a yet another embodiment, a solid pharmaceutical composition of the invention comprises:

(1) a first type of mini-tablets, each of which is no more than 2 mm in size and comprises an amorphous solid dispersion including (i) Compound 1 or a pharmaceutically acceptable salt thereof, (ii) a pharmaceutically acceptable hydrophilic polymer and (iii) a pharmaceutically acceptable surfactant; and (2) a second type of mini-tablets, each of which is no more than 2 mm in size and comprises an amorphous solid dispersion including (i) Compound 2 or a pharmaceutically acceptable salt thereof, (ii) a pharmaceutically acceptable hydrophilic polymer and (iii) a pharmaceutically acceptable surfactant.

In a yet another embodiment, a solid pharmaceutical composition of the invention comprises:

(1) a first type of mini-tablets, each of which is no more than 5 mm in size and comprises an amorphous solid dispersion including (i) Compound 1, (ii) a pharmaceutically acceptable hydrophilic polymer and (iii) a pharmaceutically acceptable surfactant, and wherein the total amount of Compound 1 comprised in the first type of mini-tablets is 100 mg; and (2) a second type of mini-tablets, each of which is no more than 5 mm in size and comprises an amorphous solid dispersion including (i) Compound 2, (ii) a pharmaceutically acceptable hydrophilic polymer and (iii) a pharmaceutically acceptable surfactant, and wherein the total amount of Compound 2 comprised in the second type of mini-tablets is 40 mg.

In a yet another embodiment, a solid pharmaceutical composition of the invention comprises:

(1) a first type of mini-tablets, each of which is no more than 3 mm in size and comprises an amorphous solid dispersion including (i) Compound 1, (ii) a pharmaceutically acceptable hydrophilic polymer and (iii) a pharmaceutically acceptable surfactant, and wherein the total amount of Compound 1 comprised in the first type of mini-tablets is 100 mg; and (2) a second type of mini-tablets, each of which is no more than 3 mm in size and comprises an amorphous solid dispersion including (i) Compound 2, (ii) a pharmaceutically acceptable hydrophilic polymer and (iii) a pharmaceutically acceptable surfactant, and wherein the total amount of Compound 2 comprised in the second type of mini-tablets is 40 mg.

In a yet another embodiment, a solid pharmaceutical composition of the invention comprises:

(1) a first type of mini-tablets, each of which is no more than 2 mm in size and comprises an amorphous solid dispersion including (i) Compound 1, (ii) a pharmaceutically acceptable hydrophilic polymer and (iii) a pharmaceutically acceptable surfactant, and wherein the total amount of Compound 1 comprised in the first type of mini-tablets is 100 mg; and (2) a second type of mini-tablets, each of which is no more than 2 mm in size and comprises an amorphous solid dispersion including (i) Compound 2, (ii) a pharmaceutically acceptable hydrophilic polymer and (iii) a pharmaceutically acceptable surfactant, and wherein the total amount of Compound 2 comprised in the second type of mini-tablets is 40 mg.

In a yet another embodiment, a solid pharmaceutical composition of the invention comprises:

(1) a first type of mini-tablets, each of which is no more than 5 mm in size and comprises an amorphous solid dispersion including (i) Compound 1, (ii) copovidone and (iii) Vitamin E TPGS, and wherein the total amount of Compound 1 comprised in the first type of mini-tablets is 100 mg; and (2) a second type of mini-tablets, each of which is no more than 5 mm in size and comprises an amorphous solid dispersion including (i) Compound 2, (ii) copovidone and (iii) Vitamin E TPGS, and wherein the total amount of Compound 2 comprised in the second type of mini-tablets is 40 mg.

In a yet another embodiment, a solid pharmaceutical composition of the invention comprises:

(1) a first type of mini-tablets, each of which is no more than 3 mm in size and comprises an amorphous solid dispersion including (i) Compound 1, (ii) copovidone and (iii) Vitamin E TPGS, and wherein the total amount of Compound 1 comprised in the first type of mini-tablets is 100 mg; and (2) a second type of mini-tablets, each of which is no more than 3 mm in size and comprises an amorphous solid dispersion including (i) Compound 2, (ii) copovidone and (iii) Vitamin E TPGS, and wherein the total amount of Compound 2 comprised in the second type of mini-tablets is 40 mg.

In a yet another embodiment, a solid pharmaceutical composition of the invention comprises:

(1) a first type of mini-tablets, each of which is no more than 2 mm in size and comprises an amorphous solid dispersion including (i) Compound 1, (ii) copovidone and (iii) Vitamin E TPGS, and wherein the total amount of Compound 1 comprised in the first type of mini-tablets is 100 mg; and (2) a second type of mini-tablets, each of which is no more than 2 mm in size and comprises an amorphous solid dispersion including (i) Compound 2, (ii) copovidone and (iii) Vitamin E TPGS, and wherein the total amount of Compound 2 comprised in the second type of mini-tablets is 40 mg.

In a yet another embodiment, a solid pharmaceutical composition of the invention comprises:

(1) a first type of mini-tablets, each of which is no more than 5 mm in size and comprises an amorphous solid dispersion including (i) Compound 1, (ii) copovidone and (iii) Vitamin E TPGS, and wherein the total amount of Compound 1 comprised in the first type of mini-tablets is 100 mg; and (2) a second type of mini-tablets, each of which is no more than 5 mm in size and comprises an amorphous solid dispersion including (i) Compound 2, (ii) copovidone and (iii) Vitamin E TPGS and propylene glycol monocaprylate, and wherein the total amount of Compound 2 comprised in the second type of mini-tablets is 40 mg.

In a yet another embodiment, a solid pharmaceutical composition of the invention comprises:

(1) a first type of mini-tablets, each of which is no more than 3 mm in size and comprises an amorphous solid dispersion including (i) Compound 1, (ii) copovidone and (iii) Vitamin E TPGS, and wherein the total amount of Compound 1 comprised in the first type of mini-tablets is 100 mg; and (2) a second type of mini-tablets, each of which is no more than 3 mm in size and comprises an amorphous solid dispersion including (i) Compound 2, (ii) copovidone and (iii) Vitamin E TPGS and propylene glycol monocaprylate, and wherein the total amount of Compound 2 comprised in the second type of mini-tablets is 40 mg.

In a yet another embodiment, a solid pharmaceutical composition of the invention comprises:

(1) a first type of mini-tablets, each of which is no more than 2 mm in size and comprises an amorphous solid dispersion including (i) Compound 1, (ii) copovidone and (iii) Vitamin E TPGS, and wherein the total amount of Compound 1 comprised in the first type of mini-tablets is 100 mg; and (2) a second type of mini-tablets, each of which is no more than 2 mm in size and comprises an amorphous solid dispersion including (i) Compound 2, (ii) copovidone and (iii) Vitamin E TPGS and propylene glycol monocaprylate, and wherein the total amount of Compound 2 comprised in the second type of mini-tablets is 40 mg.

Preferably, in any aspect, embodiment, example, preference and composition of the invention, the total weight of Compound 1 in amorphous solid dispersion ranges from 10% to 40% by weight relative to the total weight of the amorphous solid dispersion. More preferably, in any aspect, embodiment, example, preference and composition of the invention, the total weight of Compound 1 in amorphous solid dispersion ranges from 15% to 30% by weight relative to the total weight of the amorphous solid dispersion. Highly preferably, in any aspect, embodiment, example, preference and composition of the invention, the total weight of Compound 1 in amorphous solid dispersion is 20% by weight relative to the total weight of the amorphous solid dispersion.

Preferably, in any aspect, embodiment, example, preference and composition of the invention, the total weight of Compound 2 in amorphous solid dispersion ranges from 5% to 20% by weight relative to the total weight of the amorphous solid dispersion. More preferably, in any aspect, embodiment, example, preference and composition of the invention, the total weight of Compound 2 in amorphous solid dispersion is 10% by weight relative to the total weight of the amorphous solid dispersion.

More preferably, in any aspect, embodiment, example, preference and composition of the invention, the total weight of Compound 1 in amorphous solid dispersion ranges from 15% to 30% by weight relative to the total weight of the amorphous solid dispersion. And the total weight of Compound 2 in amorphous solid dispersion ranges from 5% to 15% by weight relative to the total weight of the amorphous solid dispersion.

Highly preferably, in any aspect, embodiment, example, preference and composition of the invention, the total weight of Compound 1 in amorphous solid dispersion is 20% by weight relative to the total weight of the amorphous solid dispersion. And the total weight of Compound 2 in amorphous solid dispersion is 10% by weight relative to the total weight of the amorphous solid dispersion.

Preferably, in any aspect, embodiment, example, preference and composition of the invention, the amorphous solid dispersion can comprise from 50% to 80% by weight, relative to the total weight of the amorphous solid dispersion, of a pharmaceutically acceptable hydrophilic polymer, and from 5% to 15% by weight, relative to the total weight of the amorphous solid dispersion, of a pharmaceutically acceptable surfactant.

Preferably, in any aspect, embodiment, example, preference and composition of the invention, the amorphous solid dispersion can comprise from 50% to 90% by weight, relative to the total weight of the amorphous solid dispersion, of a pharmaceutically acceptable hydrophilic polymer, and from 5% to 15% by weight, relative to the total weight of the amorphous solid dispersion, of a pharmaceutically acceptable surfactant.

Also preferably, in any aspect, embodiment, example, preference and composition of the invention, the amorphous solid dispersion can comprise from 60% to 80% by weight, relative to the total weight of the amorphous solid dispersion, of a pharmaceutically acceptable hydrophilic polymer, and 10% by weight, relative to the total weight of the amorphous solid dispersion, of a pharmaceutically acceptable surfactant.

In any aspect, embodiment, example, preference and composition of the invention, the pharmaceutically acceptable hydrophilic polymer can have a $T_g$ of at least 50° C.; preferably, the pharmaceutically acceptable hydrophilic polymer has a $T_g$ of at least 80° C.; more preferably, the pharmaceutically acceptable hydrophilic polymer has a $T_g$ of at least 100° C. For example, the pharmaceutically acceptable hydrophilic polymer can have a $T_g$ of from 80° C. to 180° C., or from 100° C. to 150° C.

Preferably, the pharmaceutically acceptable hydrophilic polymer employed in the present invention is water-soluble. A solid pharmaceutical composition of the invention can also comprise poorly water-soluble or water-insoluble polymers, such as cross-linked polymers. The pharmaceutically acceptable hydrophilic polymer comprised in a solid pharmaceutical composition of the invention preferably has an apparent viscosity, when dissolved at 20° C. in an aqueous solution at 2% (w/v), of 1 to 5000 mPa·s., and more preferably of 1 to 700 mPa·s, and most preferably of 5 to 100 mPa·s.

In any aspect, embodiment, example and composition of the invention, the pharmaceutically acceptable hydrophilic polymer can be selected from homopolymer of N-vinyl lactam, copolymer of N-vinyl lactam, cellulose ester, cellulose ether, polyalkylene oxide, polyacrylate, polymethacrylate, polyacrylamide, polyvinyl alcohol, vinyl acetate polymer, oligosaccharide, polysaccharide, or combinations thereof. Non-limiting examples of suitable hydrophilic polymers include homopolymer of N-vinyl pyrrolidone, copolymer of N-vinyl pyrrolidone, copolymer of N-vinyl pyrrolidone and vinyl acetate, copolymer of N-vinyl pyrrolidone and vinyl propionate, polyvinylpyrrolidone, methylcellulose, ethylcellulose, hydroxyalkylcelluloses, hydroxypropylcellulose, hydroxyalkylalkylcellulose, hydroxypropylmethylcellulose, cellulose phthalate, cellulose succinate, cellulose acetate phthalate, hydroxypropylmethylcellulose phthalate, hydroxypropylmethylcellulose succinate, hydroxypropylmethylcellulose acetate succinate, polyethylene oxide, polypropylene oxide, copolymer of ethylene oxide and propylene oxide, methacrylic acid/ethyl acrylate copolymer, methacrylic acid/methyl methacrylate copolymer, butyl methacrylate/2-dimethylaminoethyl methacrylate copolymer, poly(hydroxyalkyl acrylate), poly(hydroxyalkyl methacrylate), copolymer of vinyl acetate and crotonic acid, partially hydrolyzed polyvinyl acetate, carrageenan, galactomannan, xanthan gum, or combinations thereof.

Preferably, in any aspect, embodiment, example, preference and composition of the invention, the polymer is copovidone.

In any aspect, embodiment, example, preference and composition of the invention, the pharmaceutically acceptable surfactant can have an HLB value of at least 10. Surfactants having an HLB value of less than 10 can also be used.

In any aspect, embodiment, example, preference and composition of the invention, the pharmaceutically acceptable surfactant can be selected from polyoxyethylene castor oil derivates, mono fatty acid ester of polyoxyethylene sorbitan, polyoxyethylene alkyl ether, polyoxyethylene alkylaryl ether, polyethylene glycol fatty acid ester, alkylene glycol fatty acid mono ester, sucrose fatty acid ester, sorbitan fatty acid mono ester, or combinations thereof. Non-limiting examples of suitable surfactants include polyoxyethyleneglycerol triricinoleate or polyoxyl 35 castor oil (Cremophor® EL; BASF Corp.) or polyoxyethyleneglycerol oxystearate such as polyethylenglycol 40 hydrogenated castor oil (Cremophor® RH 40, also known as polyoxyl 40 hydrogenated castor oil or macrogolglycerol hydroxystearate) or polyethylenglycol 60 hydrogenated castor oil (Cremophor® RH 60), mono fatty acid ester of polyoxyethylene sorbitan, such as mono fatty acid ester of polyoxyethylene (20) sorbitan, e.g. polyoxyethylene (20) sorbitan monooleate (Tween® 80), polyoxyethylene (20) sorbitan monostearate (Tween® 60), polyoxyethylene (20) sorbitan monopalmitate (Tween® 40) or polyoxyethylene (20) sorbitan monolaurate (Tween® 20), polyoxyethylene (3) lauryl ether, polyoxyethylene (5) cetyl ether, polyoxyethylene (2) stearyl ether, polyoxyethylene (5) stearyl ether, polyoxyethylene (2) nonylphenyl ether, polyoxyethylene (3) nonylphenyl ether, polyoxyethylene (4) nonylphenyl ether, polyoxyethylene (3) octylphenyl ether, PEG-200 monolaurate, PEG-200 dilaurate, PEG-300 dilaurate, PEG-400 dilaurate, PEG-300 distearate, PEG-300 dioleate, propylene glycol monolaurate (e.g., Lauroglycol), sucrose monostearate, sucrose distearate, sucrose monolaurate, sucrose dilaurate, sorbitan mono laurate, sorbitan monooleate, sorbitan monopalnitate, sorbitan stearate, or combinations thereof.

Preferably, in any aspect, embodiment, example, preference and composition of the invention, the pharmaceutically acceptable surfactant is or includes D-alpha-tocopheryl polyethylene glycol 1000 succinate (vitamin E TPGS).

Also preferably, in any aspect, embodiment, example, preference and composition of the invention, the pharmaceutically acceptable surfactant used in the amorphous solid dispersion comprising Compound 2 is or includes a combination of Vitamin E TPGS and propylene glycol monocaprylate.

Highly preferably, in any aspect, embodiment, example, preference and composition of the invention, the pharmaceutically acceptable hydrophilic polymer is copovidone, and the pharmaceutically acceptable surfactant is or includes vitamin E TPGS.

In any aspect, embodiment, example, preference and composition of the invention, the amorphous solid dispersion preferably comprises or consists of a single-phase (defined in thermodynamics) in which Compound 1 or Compound 2 is amorphously dispersed in a matrix containing the pharmaceutically acceptable hydrophilic polymer and the pharmaceutically acceptable surfactant. Thermal analysis of the amorphous solid dispersion using differential scanning calorimetry (DSC) typically shows only one single $T_g$, and the amorphous solid dispersion typically does not contain any detectable crystalline compound as measured by X-ray powder diffraction spectroscopy.

In any aspect, embodiment, example, preference and composition of the invention, the solid pharmaceutical composition of the invention can be a tablet.

In any aspect, embodiment, example, preference and composition of the invention, the solid pharmaceutical composition of the invention can be a mixture of mini-tablets.

In any aspect, embodiment, example, preference and composition of the invention, the solid pharmaceutical composition of the invention can be prepared into other suitable dosage forms, such as capsule, dragee, granule, or powder.

In any aspect, embodiment, example, preference and composition of the invention, the solid pharmaceutical composition of the invention is administered to a HCV patient with food to treat HCV. Administration with food can significantly improve the bioavailability of Compound 1 and Compound 2 in the patient when delivered using the solid pharmaceutical composition of the invention.

A solid pharmaceutical composition of the invention can further comprise another anti-HCV agent, for example, an agent selected from HCV helicase inhibitors, HCV polymerase inhibitors, HCV protease inhibitors, HCV NS5A inhibitors, CD81 inhibitors, cyclophilin inhibitors, or internal ribosome entry site (IRES) inhibitors.

Any composition of the invention, as described or contemplated herein (e.g., the compositions described in Examples 1 and 2), preferably has the following in vitro release profile: when dissolved in 1000 mL of a dissolution medium using a standard USP dissolution Apparatus 2 (paddle) with Japanese sinker operating at 75 RPM at 37° C., at least 80% of Compound 1 in the composition is released within 3 hours and at least 80% of Compound 2 in the composition is released within 3 hours, wherein the dissolution medium is 0.1 M Acetate buffer (pH 4.0) with 1% Polysorbate 80.

Any composition of the invention, as described or contemplated herein (e.g., the compositions described in Examples 1 and 2), preferably has the following in vitro release profile: when dissolved in 1000 mL of a dissolution medium using a standard USP dissolution Apparatus 2 (paddle) with Japanese sinker operating at 75 RPM at 37° C., at least 90% of Compound 1 in the composition is released within 3 hours and at least 90% of Compound 2 in the composition is released within 3 hours, wherein the dissolution medium is 0.1 M Acetate buffer (pH 4.0) with 1% Polysorbate 80.

Any composition of the invention, as described or contemplated herein (e.g., the compositions described in Examples 1 and 2), preferably has the following in vitro release profile: when dissolved in 1000 mL of a dissolution medium using a standard USP dissolution Apparatus 2 (paddle) with Japanese sinker operating at 75 RPM at 37° C., at least 75% of Compound 1 in the composition is released within 105 minutes and at least 80% of Compound 2 in the composition is released within 105 minutes, wherein the dissolution medium is 0.1 M Acetate buffer (pH 4.0) with 1% Polysorbate 80.

Any composition of the invention, as described or contemplated herein (e.g., the compositions described in Examples 1 and 2), preferably has the following in vitro release profile: when dissolved in 1000 mL of a dissolution medium using a standard USP dissolution Apparatus 2 (paddle) with Japanese sinker operating at 75 RPM at 37° C., at least 80% of Compound 1 in the composition is released within 100 minutes and at least 80% of Compound 2 in the composition is released within 100 minutes, wherein the dissolution medium is 0.1 M Acetate buffer (pH 4.0) with 1% Polysorbate 80.

Any composition of the invention, as described or contemplated herein (e.g., the compositions described in Examples 1 and 2), preferably has the following in vitro release profile: when dissolved in 1000 mL of a dissolution medium using a standard USP dissolution Apparatus 2 (paddle) with Japanese sinker operating at 75 RPM at 37° C., at least 40% of Compound 1 in the composition is released within 50 minutes and at least 50% of Compound 2 in the composition is released within 50 minutes, wherein the dissolution medium is 0.1 M Acetate buffer (pH 4.0) with 1% Polysorbate 80.

Any composition of the invention, as described or contemplated herein (e.g., the compositions described in Examples 1 and 2), preferably has the following in vitro release profile: when dissolved in 1000 mL of a dissolution medium using a standard USP dissolution Apparatus 2 (paddle) with Japanese sinker operating at 75 RPM at 37° C., at least 30% of Compound 1 in the composition is released within 50 minutes and at least 45% of Compound 2 in the composition is released within 50 minutes, wherein the dissolution medium is 0.1 M Acetate buffer (pH 4.0) with 1% Polysorbate 80.

Any composition of the invention, as described or contemplated herein (e.g., the compositions described in Examples 1 and 2), preferably has the following in vitro release profile: when dissolved in 1000 mL of a dissolution medium using a standard USP dissolution Apparatus 2 (paddle) with Japanese sinker operating at 75 RPM at 37° C., at least 10% of Compound 1 in the composition is released within 25 minutes and at least 20% of Compound 2 in the composition is released within 25 minutes, wherein the dissolution medium is 0.1 M Acetate buffer (pH 4.0) with 1% Polysorbate 80.

Any composition of the invention, as described or contemplated herein (e.g., the compositions described in Examples 1 and 2), preferably has the following in vitro release profile: when dissolved in 1000 mL of a dissolution medium using a standard USP dissolution Apparatus 2 (paddle) with Japanese sinker operating at 75 RPM at 37° C., at least 5% of Compound 1 in the composition is released within 25 minutes and at least 10% of Compound 2 in the composition is released within 25 minutes, wherein the dissolution medium is 0.1 M Acetate buffer (pH 4.0) with 1% Polysorbate 80.

Any composition of the invention, as described or contemplated herein (e.g., the compositions described in Examples 1 and 2), preferably has the following in vitro release profile: when dissolved in 1000 mL of a dissolution medium using a standard USP dissolution Apparatus 2 (paddle) with Japanese sinker operating at 75 RPM at 37° C., 80-100% of Compound 1 in the composition is released within 3 hours and at least 80-100% of Compound 2 in the composition is released within 3 hours, wherein the dissolution medium is 0.1 M Acetate buffer (pH 4.0) with 1% Polysorbate 80.

Any composition of the invention, as described or contemplated herein (e.g., the compositions described in Examples 1 and 2), preferably has the following in vitro release profile: when dissolved in 1000 mL of a dissolution medium using a standard USP dissolution Apparatus 2 (paddle) with Japanese sinker operating at 75 RPM at 37° C., 90-100% of Compound 1 in the composition is released within 3 hours and at least 90-100% of Compound 2 in the composition is released within 3 hours, wherein the dissolution medium is 0.1 M Acetate buffer (pH 4.0) with 1% Polysorbate 80.

Any composition of the invention, as described or contemplated herein (e.g., the compositions described in Examples 1 and 2), preferably has the following in vitro release profile: when dissolved in 1000 mL of a dissolution medium using a standard USP dissolution Apparatus 2 (paddle) with Japanese sinker operating at 75 RPM at 37° C., 75-100% of Compound 1 in the composition is released within 105 minutes and 80-100% of Compound 2 in the composition is released within 105 minutes, wherein the dissolution medium is 0.1 M Acetate buffer (pH 4.0) with 1% Polysorbate 80.

Any composition of the invention, as described or contemplated herein (e.g., the compositions described in Examples 1 and 2), preferably has the following in vitro release profile: when dissolved in 1000 mL of a dissolution medium using a standard USP dissolution Apparatus 2 (paddle) with Japanese sinker operating at 75 RPM at 37° C., 80-100% of Compound 1 in the composition is released within 100 minutes and 85-100% of Compound 2 in the composition is released within 100 minutes, wherein the dissolution medium is 0.1 M Acetate buffer (pH 4.0) with 1% Polysorbate 80.

Any composition of the invention, as described or contemplated herein (e.g., the compositions described in Examples 1 and 2), preferably has the following in vitro release profile: when dissolved in 1000 mL of a dissolution medium using a standard USP dissolution Apparatus 2 (paddle) with Japanese sinker operating at 75 RPM at 37° C., 40-60% of Compound 1 in the composition is released within 50 minutes and 50-80% of Compound 2 in the composition is released within 50 minutes, wherein the dissolution medium is 0.1 M Acetate buffer (pH 4.0) with 1% Polysorbate 80.

Any composition of the invention, as described or contemplated herein (e.g., the compositions described in Examples 1 and 2), preferably has the following in vitro release profile: when dissolved in 1000 mL of a dissolution medium using a standard USP dissolution Apparatus 2 (paddle) with Japanese sinker operating at 75 RPM at 37° C., 30-60% of Compound 1 in the composition is released within 50 minutes and 45-80% of Compound 2 in the composition is released within 50 minutes, wherein the dissolution medium is 0.1 M Acetate buffer (pH 4.0) with 1% Polysorbate 80.

Any composition of the invention, as described or contemplated herein (e.g., the compositions described in Examples 1 and 2), preferably has the following in vitro release profile: when dissolved in 1000 mL of a dissolution medium using a standard USP dissolution Apparatus 2 (paddle) with Japanese sinker operating at 75 RPM at 37° C., 10-30% of Compound 1 in the composition is released within 25 minutes and 20-40% of Compound 2 in the composition is released within 25 minutes, wherein the dissolution medium is 0.1 M Acetate buffer (pH 4.0) with 1% Polysorbate 80.

Any composition of the invention, as described or contemplated herein (e.g., the compositions described in Examples 1 and 2), preferably has the following in vitro release profile: when dissolved in 1000 mL of a dissolution medium using a standard USP dissolution Apparatus 2 (paddle) with Japanese sinker operating at 75 RPM at 37° C., 5-30% of Compound 1 in the composition is released within 25 minutes and 10-40% of Compound 2 in the composition is released within 25 minutes, wherein the dissolution medium is 0.1 M Acetate buffer (pH 4.0) with 1% Polysorbate 80.

Any composition of the invention, as described or contemplated herein (e.g., the compositions described in Examples 1 and 2), preferably has the following in vitro release profile: when dissolved in 1000 mL of a dissolution medium using a standard USP dissolution Apparatus 2 (paddle) with Japanese sinker operating at 75 RPM at 37° C., 10-30% of Compound 1 in the composition is released within 25 minutes and 20-40% of Compound 2 in the composition is released within 25 minutes, 40-60% of Compound 1 in the composition is released within 50 minutes and 50-80% of Compound 2 in the composition is released within 50 minutes, 80-100% of Compound 1 in the composition is released within 100 minutes and 85-100% of Compound 2 in the composition is released within 100 minutes, wherein the dissolution medium is 0.1 M Acetate buffer (pH 4.0) with 1% Polysorbate 80.

Any composition of the invention, as described or contemplated herein (e.g., the compositions described in Examples 1 and 2), preferably has the following in vitro release profile: when dissolved in 1000 mL of a dissolution medium using a standard USP dissolution Apparatus 2 (paddle) with Japanese sinker operating at 75 RPM at 37° C., 5-30% of Compound 1 in the composition is released within 25 minutes and 10-40% of Compound 2 in the composition is released within 25 minutes, 30-60% of Compound 1 in the composition is released within 50 minutes and 45-80% of Compound 2 in the composition is released within 50 minutes, 75-100% of Compound 1 in the composition is released within 105 minutes and 80-100% of Compound 2 in the composition is released within 105 minutes, wherein the dissolution medium is 0.1 M Acetate buffer (pH 4.0) with 1% Polysorbate 80.

In another aspect, the present invention features processes of making a solid pharmaceutical composition of the invention. The processes comprise (1) preparing a melt comprising a compound of interest, a pharmaceutically acceptable hydrophilic polymer, and a pharmaceutically acceptable surfactant; and (2) solidifying said melt. The solidified melt can comprise any amorphous solid dispersion described or contemplated herein. As used herein, a "compound of interest" refers to Compound 1 or a pharmaceutically acceptable salt thereof, or Compound 2 or a pharmaceutically acceptable salt thereof. The processes can further comprise milling the solidified melt, followed by compressing the milled product with one or more other excipients or ingredients (e.g., blending the milled product with one or more other excipients or ingredients and then compressing the blend mixture) to form a tablet, a mini-tablet, or a layer in atablet. These other excipients or ingredients can include, for example, coloring agents, flavoring agents, lubricants or preservatives. Film-coating can also be added to the tablet or mini-tablet thus prepared.

In one embodiment, the melt is formed at a temperature of from 150 to 180° C. In another embodiment, the melt is formed at a temperature of from 150 to 170° C. In yet another embodiment, the melt is formed at a temperature of from 150 to 160° C. In yet another embodiment, the melt is formed at a temperature of from 160 to 170° C.

Any amorphous solid dispersion described or contemplated herein, including any amorphous solid dispersion described or contemplated in any aspect, embodiment, example, preference and composition of the invention, can be prepared according to any process described or contemplated herein.

In still another aspect, the present invention features solid pharmaceutical compositions prepared according to a process of the invention. Any process described or contemplated herein can be used to prepare a solid pharmaceutical composition comprising a compound of interest, a pharmaceutically acceptable hydrophilic polymer, and a pharmaceutically acceptable surfactant.

The present invention further features methods of using a solid pharmaceutical composition of the invention to treat HCV infection. The methods comprise administering a solid pharmaceutical composition of the invention to a patient in need thereof. The patient can be infected with HCV genotype 1, 2, 3, 4, 5 or 6.

The amorphous solid dispersion employed in the present invention can be prepared by a variety of techniques such as, without limitation, melt-extrusion, spray-drying, co-precipitation, freeze drying, or other solvent evaporation techniques, with melt-extrusion and spray-drying being preferred. The melt-extrusion process typically comprises the steps of preparing a melt which includes the active ingredient(s), the pharmaceutically acceptable hydrophilic polymer(s) and preferably the pharmaceutically acceptable surfactant(s), and then cooling the melt until it solidifies. "Melting" means a transition into a liquid or rubbery state in which it is possible for one component to get embedded, preferably homogeneously embedded, in the other component or components. In many cases, the polymer component(s) will melt and the other components including the active ingredient(s) and surfactant(s) will dissolve in the melt thereby forming a solution. Melting usually involves heating above the softening point of the polymer(s). The preparation of the melt can take place in a variety of ways. The mixing of the components can take place before, during or after the formation of the melt. For example, the components can be mixed first and then melted or be simultaneously mixed and melted. The melt can also be homogenized in order to disperse the active ingredient(s) efficiently. In addition, it may be convenient first to melt the polymer(s) and then to mix in and homogenize the active ingredient(s). In one example, all materials except surfactant(s) are blended and fed into an extruder, while the pharmaceutically acceptable surfactant(s) is molten externally and pumped in during extrusion.

To start a melt-extrusion process, the active ingredient(s) (e.g., Compound 1 or Compound 2) can be employed in their solid forms, such as their respective crystalline forms. The active ingredient(s) can also be employed as a solution or dispersion in a suitable liquid solvent such as alcohols, aliphatic hydrocarbons, esters or, in some cases, liquid carbon dioxide. The solvent can be removed, e.g. evaporated, upon preparation of the melt.

Various additives can also be included in the melt, for example, flow regulators (e.g., colloidal silica), binders, lubricants, fillers, disintegrants, plasticizers, colorants, or stabilizers (e.g., antioxidants, light stabilizers, radical scavengers, and stabilizers against microbial attack).

The melting and/or mixing can take place in an apparatus customary for this purpose. Particularly suitable ones are extruders or kneaders. Suitable extruders include single screw extruders, intermeshing screw extruders or multi-screw extruders, preferably twin screw extruders, which can be corotating or counterrotating and, optionally, be equipped with kneading disks. It will be appreciated that the working temperatures will be determined by the kind of extruder or the kind of configuration within the extruder that is used. Part of the energy needed to melt, mix and dissolve the components in the extruder can be provided by heating elements. However, the friction and shearing of the material in the extruder may also provide a substantial amount of energy to the mixture and aid in the formation of a homogeneous melt of the components.

The melt can range from thin to pasty to viscous. Shaping of the extrudate can be conveniently carried out by a calender with two counter-rotating rollers with mutually matching depressions on their surface. The extrudate can be cooled and allowed to solidify. The extrudate can also be cut into pieces, either before (hot-cut) or after solidification (cold-cut).

The solidified extrusion product can be further milled, ground or otherwise reduced to granules. The solidified extrudate, as well as each granule produced, comprises a solid dispersion, preferably a solid solution, of the active ingredient(s) in a matrix comprised of the pharmaceutically acceptable hydrophilic polymer(s) and the pharmaceutically acceptable surfactant(s). The extrusion product can also be blended with other active ingredient(s) and/or additive(s) before being milled or ground to granules. The granules can be further processed into suitable solid oral dosage forms.

In one example, copovidone and one or more surfactants (e.g., vitamin E TPGS) are mixed and granulated, followed by the addition of aerosil and a compound of interest. The mixture is milled, and then subject to extrusion. The extrudate thus produced can be milled and sieved for further processing to make capsules or tablets or mini-tablets. Surfactant(s) employed in this example can be added, for example, through liquid dosing during extrusion.

Preferably, in any aspect, embodiment, example, preference and composition of the invention where Compound 1 and Compound 2 are comprised in separate layers in a tablet, Compound 1 is melt-extruded at a temperature of from 155 to 180° C., and Compound 2 is melt-extruded at a temperature of from 150 to 195° C. For these cases, Compound 2 can also be melt-extruded at a temperature of from 150 to less than 222° C.

The generation of an acceptable amorphous Compound 2 extrudate has been found difficult. For instance, the particle size distribution (PSD) of the crystalline Compound 2 used for extrusion was shown to have a significant impact on extrudate appearance: the larger the particles the higher the risk to obtain a turbid extrudate with residual crystallinity. Therefore, preferably, in any aspect, embodiment, example, preference and composition of the invention where Compound 1 and Compound 2 are comprised in separate layers in a tablet, before melt-extrusion, the crystalline Compound 2 is milled to particles with a median particle size (D50) of no more than 15 μm. More preferably, in any aspect, embodiment, example, preference and composition of the invention where Compound 1 and Compound 2 are comprised in separate layers in a tablet, before melt-extrusion, the crystalline Compound 2 is milled to particles with a median particle size (D50) of no more than 10 μm. Highly preferably, in any aspect, embodiment, example, preference and composition of the invention where Compound 1 and Compound 2 are comprised in separate layers in a tablet, before melt-extrusion, the crystalline Compound 2 is milled to particles with a median particle size of no more than 9 μm.

Also, preferably, in any aspect, embodiment, example, preference and composition of the invention where Compound 1 and Compound 2 are comprised in separate layers in a tablet, before melt-extrusion, the crystalline Compound 2 is milled to particles with a D90 of no more than 100 μm. More preferably, in any aspect, embodiment, example, preference and composition of the invention where Compound 1 and Compound 2 are comprised in separate layers in a tablet, before melt-extrusion, the crystalline Compound 2 is milled to particles with a D90 of no more than 80 μm. Highly preferably, in any aspect, embodiment, example, preference and composition of the invention where Compound 1 and Compound 2 are comprised in separate layers in a tablet, before melt-extrusion, the crystalline Compound 2 is milled to particles with a D90 of no more than 60 μm.

Preferably, in any aspect, embodiment, example, preference and composition of the invention where Compound 1 and Compound 2 are comprised in separate layers in a tablet, before melt-extrusion, the crystalline Compound 2 is milled to particles with a D50 of no more than 15 μm and a D90 of no more than 100 μm. More preferably, in any aspect, embodiment, example, preference and composition of the invention where Compound 1 and Compound 2 are comprised in separate layers in a tablet, before melt-extrusion, the crystalline Compound 2 is milled to particles with a D50 of no more than 10 μm and a D90 of no more than 80 μm. Highly preferably, in any aspect, embodiment, example, preference and composition of the invention where Compound 1 and Compound 2 are comprised in separate layers in a tablet, before melt-extrusion, the crystalline Compound 2 is milled to particles with a D50 of no more than 9 μm and a D90 of no more than 60 μm.

As used herein, particle size is measured by laser diffraction with Mastersizer. D90 refers to the particle size below which 90% of the particles exist.

The approach of solvent evaporation, via spray-drying, provides the advantage of allowing for processability at lower temperatures, if needed, and allows for other modifications to the process in order to further improve powder properties. The spray-dried powder can then be formulated further, if needed, and final drug product is flexible with regards to whether capsule, tablet, mini-tablet or any other solid dosage form is desired.

Exemplary spray-drying processes and spray-drying equipment are described in K. Masters, SPRAY DRYING HANDBOOK (Halstead Press, New York, $4^{th}$ ed., 1985). Non-limiting examples of spray-drying devices that are suitable for the present invention include spray dryers manufactured by Niro Inc. or GEA Process Engineering Inc., Buchi Labortechnik AG, and Spray Drying Systems, Inc. A spray-drying process generally involves breaking up a liquid mixture into small droplets and rapidly removing solvent from the droplets in a container (spray drying apparatus) where there is a strong driving force for evaporation of solvent from the droplets. Atomization techniques include, for example, two-fluid or pressure nozzles, or rotary atomizers. The strong driving force for solvent evaporation can be provided, for example, by maintaining the partial pressure of solvent in the spray drying apparatus well below the vapor pressure of the solvent at the temperatures of the drying droplets. This may be accomplished by either (1) maintaining the pressure in the spray drying apparatus at a partial vacuum; (2) mixing the liquid droplets with a warm drying gas (e.g., heated nitrogen); or (3) both.

The temperature and flow rate of the drying gas, as well as the spray dryer design, can be selected so that the droplets are dry enough by the time they reach the wall of the apparatus. This help to ensure that the dried droplets are essentially solid and can form a fine powder and do not stick to the apparatus wall. The spray-dried product can be collected by removing the material manually, pneumatically, mechanically or by other suitable means. The actual length of time to achieve the preferred level of dryness depends on the size of the droplets, the formulation, and spray dryer operation. Following the solidification, the solid powder may stay in the spray drying chamber for additional time (e.g., 5-60 seconds) to further evaporate solvent from the solid powder. The final solvent content in the solid dispersion as it exits the dryer is preferably at a sufficiently low level so as to improve the stability of the final product. For instance, the residual solvent content of the spray-dried powder can be less than 2% by weight. Highly preferably, the residual solvent content is within the limits set forth in the International Conference on Harmonization (ICH) Guidelines. In addition, it may be useful to subject the spray-dried composition to further drying to lower the residual solvent to even lower levels. Methods to further lower solvent levels include, but are not limited to, fluid bed drying, infra-red drying, tumble drying, vacuum drying, and combinations of these and other processes.

Like the solid extrudate described above, the spray dried product contains a solid dispersion, preferably a solid solution, of the active ingredient(s) in a matrix comprised of the pharmaceutically acceptable hydrophilic polymer(s) and the pharmaceutically acceptable surfactant(s).

Before feeding into a spray dryer, the active ingredient(s) (e.g., Compound 1 or Compound 2), the pharmaceutically acceptable hydrophilic polymer(s), as well as other excipients such as the pharmaceutically acceptable surfactant(s), can be dissolved in a solvent. Suitable solvents include, but are not limited to, alkanols (e.g., methanol, ethanol, 1-propanol, 2-propanol or mixtures thereof), acetone, acetone/water, alkanol/water mixtures (e.g., ethanol/water mixtures), or combinations thereof. The solution can also be preheated before being fed into the spray dryer.

The solid dispersion produced by melt-extrusion, spray-drying or other techniques can be prepared into any suitable solid oral dosage forms. In one embodiment, the solid dispersion prepared by melt-extrusion, spray-drying or other techniques (e.g., the extrudate or the spray-dried powder) can be compressed into tablets or mini-tablets. The solid dispersion can be either directly compressed, or milled or ground to granules or powders before compression. Compression can be done in a tablet press, such as in a steel die between two moving punches.

At least one additive selected from flow regulators, binders, lubricants, fillers, disintegrants, or plasticizers may be used in compressing the solid dispersion. These additives can be mixed with ground or milled solid dispersion before compacting. Disintegrants promote a rapid disintegration of the compact in the stomach and keeps the liberated granules separate from one another. Non-limiting examples of suitable disintegrants are cross-linked polymers such as cross-linked polyvinyl pyrrolidone, cross-linked sodium carboxymethylcellulose or sodium croscarmellose. Non-limiting examples of suitable fillers (also referred to as bulking agents) are lactose monohydrate, calcium hydrogenphosphate, microcrystalline cellulose (e.g., Avicell), silicates, in particular silicium dioxide, magnesium oxide, talc, potato or corn starch, isomalt, or polyvinyl alcohol. Non-limiting examples of suitable flow regulators include highly dispersed silica (e.g., colloidal silica such as Aerosil), and animal or vegetable fats or waxes. Non-limiting examples of suitable lubricants include polyethylene glycol (e.g., having a molecular weight of from 1000 to 6000), magnesium and calcium stearates, sodium stearyl fumarate, and the like.

Various other additives or ingredients may also be used in preparing a solid composition of the present invention, for example dyes such as azo dyes, organic or inorganic pigments such as aluminium oxide or titanium dioxide, or dyes of natural origin; stabilizers such as antioxidants, light stabilizers, radical scavengers, stabilizers against microbial attack; or other active pharmaceutical ingredients.

In order to facilitate the intake of a solid dosage form, it is advantageous to give the dosage form an appropriate shape. Large tablets that can be swallowed comfortably are therefore preferably elongated rather than round in shape.

A film coat on the tablet further contributes to the ease with which it can be swallowed. A film coat also improves taste and provides an elegant appearance. The film-coat usually includes a polymeric film-forming material such as polyvinyl alcohol, hydroxypropyl methylcellulose, hydroxypropylcellulose, and acrylate or methacrylate copolymers. Besides a film-forming polymer, the film-coat may further comprise a plasticizer, e.g. polyethylene glycol, a surfactant, e.g. polysorbates, and optionally a pigment, e.g. titanium dioxide or iron oxides. For instance, titanium dioxide can be used as an opacifier; and/or iron oxide red can be used as a colorant. The film-coating can also comprise a filler, e.g., lactose. The film-coating may also comprise talc as anti-adhesive. Preferably, the film coat accounts for less than 5% by weight of a pharmaceutical composition of the present invention. Higher amounts of the film coating can also be used.

All mini-tablets employed in the present invention can also be film coated. Preferably, the film coat accounts for no more than 30% by weight of each mini-tablet. More preferably, the film coat accounts for 10-20% by weight of each mini-tablet.

The present invention also unexpectedly found that in order for the mini-tablets described herein to provide adequate bioavailability similar to that of a regular tablet containing the same amount of drug in the same solid dispersion formulation, the mini-tablets need to be administered with food. Human clinical studies showed that food can significantly increase bioavailability of Compound 1 and Compound 2 formulated in mini-tablets and in solid dispersion form. For instance, without food, mini-tablets containing 200 mg Compound 1 provided an AUC that was 41% lower than that provided by two regular tablets that contained the same amount of Compound 1 in the same solid dispersion formulation as in the mini-tablets. In comparison, when administered with food, the mini-tablets provided an AUC that was only 5% lower than that provided by the regular tablets. Likewise, when administered without food, mini-tablets containing 120 mg Compound 2 provided an AUC that was 28% lower than that provided by three regular tablets that contained the same amount of Compound 2 in the same solid dispersion formulation as in the mini-tablets; however, when administered with food, the mini-tablets provided an AUC that was 6% higher than that provided by the regular tablets. All of the reference AUCs of the regular tablets were measured under fasting conditions.

Accordingly, the present invention features methods of treating HCV infection, wherein the methods comprise administering with food to a patient in need thereof a solid pharmaceutical composition of the invention that contains mini-tablets, such that the ratio of the Compound 1 AUC provided by the solid pharmaceutical composition over the Compound 1 AUC provided by a regular tablet comprising the same amount of Compound 1 in the same solid dispersion formulation as in the solid pharmaceutical composition is from 0.8 to 1.25, and the ratio of the Compound 2 AUC provided by the solid pharmaceutical composition over the Compound 2 AUC provided by a regular tablet comprising the same amount of Compound 2 in the same solid dispersion formulation as in the solid pharmaceutical composition is from 0.8 to 1.25. All AUCs are human AUCs, and all AUCs of the regular tablets are measured when the regular tablets are administered under fasting condition. Any composition described herein that contains mini-tablets can be used in these methods. The patient can be infected with HCV genotype 1, 2, 3, 4, 5 or 6.

In another aspect, the present invention features methods of treating HCV infection, wherein the methods comprise administering with food to a patient in need thereof a solid pharmaceutical composition of the invention that contains mini-tablets, such that the ratio of the Compound 1 AUC provided by the solid pharmaceutical composition over the Compound 1 AUC provided by a regular tablet comprising the same amount of Compound 1 (e.g., 100 mg) in the same solid dispersion formulation as in the solid pharmaceutical composition is from 0.8 to 1.25, and the ratio of the Compound 2 AUC provided by the solid pharmaceutical composition over the Compound 2 AUC provided by a regular tablet comprising the same amount of Compound 2 (e.g., 40 mg) in the same solid dispersion formulation as in the solid pharmaceutical composition is from 0.8 to 1.25. All AUCs are human AUCs, and all AUCs of the regular tablets are measured when the regular tablets are administered under fasting condition. Any composition described herein that contains mini-tablets can be used in these methods. The patient can be infected with HCV genotype 1, 2, 3, 4, 5 or 6.

It should be understood that the above-described embodiments and the following examples are given by way of illustration, not limitation. Various changes and modifications within the scope of the present invention will become apparent to those skilled in the art from the present description.

Example 1. Bilayer Film Coated Tablet 100 mg Compound 1 and 40 mg Compound 2 are prepared into a bilayer film-coated tablet. The composition of the bilayer film-coated tablet is shown in Table 1a or Table 1b. The tablet core consists of two layers, each based on an extrudate intermediate comprising Compound 1 (Table 2), and Compound 2 (Table 3), respectively. The compressed tablets are film-coated with a coating formulation based on hypromellose as non-functional coating.

TABLE 1a

Composition of Compound 1/Compound 2, 100 mg/40 mg Bilayer Film-Coated Tablet

| Ingredient | Amount (mg) |
|---|---|
| Compound 1, 20% extrusion granulation (see Table 2) | 500 |
| Compound 2, 10% extrusion granulation (see Table 3) | 400 |
| Croscarmellose sodium, Type Ac-Di-Sol ® | 26.3 |
| Colloidal silicon dioxide, Type Aerosil ® 200 | 4.7 |
| Sodium stearyl fumarate, Type Pruv ® | 4.7 |
| HPMC Coating | 37.4 |
| Total film-coated tablet | 973.1 |

TABLE 1b

Composition of Compound 1/Compound 2, 100 mg/40 mg Bilayer Film-Coated Tablet

| Ingredient | Amount (mg) |
|---|---|
| Compound 1, 20% extrusion granulation (see Table 2) | 500 |
| Compound 2, 10% extrusion granulation (see Table 3) | 400 |
| Croscarmellose sodium, Type Ac-Di-Sol ® | 26.3 |
| Colloidal silicon dioxide, Type Aerosil ® 200 | 4.7 |
| Sodium stearyl fumarate, Type Pruv ® | 4.7 |
| HPMC Coating | 28.1 |
| Total film-coated tablet | 963.8 |

TABLE 2

Composition of Compound 1, 20% Extrusion Granulation

| Ingredient | Amount (%, w/w) |
|---|---|
| Compound 1 | 20 |
| Copovidone, Type K 28 | 69 |
| Vitamin E Polyethylene Glycol Succinate (Vitamin E TPGS) | 10 |
| Colloidal silicon dioxide, Type Aerosil ® 200 | 1 |
| Total | 100 |

TABLE 3

Composition of Compound 2, 10% Extrusion Granulation

| Ingredient | Amount (%, w/w) |
|---|---|
| Compound 2 | 10. |
| Copovidon, Type K 28 | 79 |
| Vitamin E Polyethylene Glycol Succinate (Vitamin E TPGS) | 8 |
| Propylene Glycol Monocaprylate, Type II (Capryol ™ 90) | 2 |
| Colloidal silicon dioxide, Type Aerosil ® 200 | 1 |
| Total | 100 |

Example 2. Mini-Tablets

Mini-tablets containing Compound 1 or Compound 2 can be prepared using the extrudates described in Tables 2 and 3 of Example 1, respectively. Manufacturing of Compound 1 mini-tablets can include the following steps: milling of the Compound 1 extrudate (e.g., the one described in Table 2 of Example 1), and then blending together with croscarmellose, colloidal silicon dioxide and sodium stearylfumarate, followed by tableting with a KORSCH XL 100 rotary press, using 19 fold 2 mm tableting tooling.

Manufacturing of Compound 2 mini-tablets can include the following steps: milling of the Compound 2 extrudate (e.g., the one described in Table 3 of Example 1), and then blending with colloidal silicon dioxide and sodium stearylfumarate, followed by tableting with a KORSCH XL 100 rotary press using, 19 fold 2 mm tableting tooling.

Example 3. Bioavailability and Effect of Food on Compound 1/Compound 2 Bilayer Tablets Phase 1, single-dose, four-period, randomized, complete crossover clinical trials were conducted to determine the bioavailability and food effect of the Compound 1/Compound 2 film-coated bilayer tablets. Tablets described in Table 1b were used in Regimens A, B and C, and separate tablets containing either Compound 1 or Compound 2 were used in Regimen D.

Subjects took a single dose of Compound 1/Compound 2 on Day 1 of each Period. There was a washout of 4 days between doses.
  i. Regimens A and D: study drugs were taken under fasting conditions.
  ii. Regimen B: study drugs were taken approximately 30 minutes after start of moderate-fat breakfast (about 30% calories from fat).
  iii. Regimen C: study drugs were taken approx. 30 minutes after start of high-fat breakfast (50% calories from fat).

The study design is summarized in Tables 4a and 4b. For Regimens A, B and C, the single dose consisted of three tablets of Table 1b, each tablet contains 100 mg/40 mg Compound 1/Compound 2. For Regimen D, the single dose contained three tablets of Compound 1, each of which contained 100 mg Compound 1, as well as three tablets of Compound 2, each of which contained 40 mg Compound 2.

TABLE 4a

Single Dose, Four-Period, Complete Crossover Clinical Study Design

| Sequence Number | Number of Subjects | Period 1 | Period 2 | Period 3 | Period 4 |
|---|---|---|---|---|---|
| I | 6 | A | B | C | D |
| II | 6 | B | D | A | C |
| III | 6 | C | A | D | B |
| IV | 5 | D | C | B | A |

TABLE 4b

Single Dose, Four-Period, Complete Crossover Clinical Study Design

| Regimen A | Single dose of Compound 1/Compound 2 film-coated bilayer tablets 300 mg/120 mg (3 × 100 mg/40 mg) given under fasting conditions |
|---|---|
| Regimen B | Single dose of Compound 1/Compound 2 film-coated bilayer tablets 300 mg/120 mg (3 × 100 mg/40 mg) given with a moderate fat breakfast |
| Regimen C | Single dose of Compound 1/Compound 2 film-coated bilayer tablets 300 mg/120 mg (3 × 100 mg/40 mg) given with a high fat breakfast |
| Regimen D | Single dose of Compound 1 tablets (300 mg, 3 × 100 mg tablets) and Compound 2 tablets (120 mg, 3 × 40 mg tablets) given under fasting conditions |

Table 5a shows the pharmacokinetic profiles of Compound 1 in these studies, as well as the food effect on the bioavailability of Compound 1. Table 5b shows the pharmacokinetic profiles of Compound 2, as well as the food effect on the bioavailability of Compound 2.

TABLE 5a

Compound 1 Pharmacokinetic Parameters ((Geometric Mean (Mean, CV %))

| Pharmacokinetic Parameters | Units | Regimen A (N = 23) | Regimen B (N = 23) | Regimen C (N = 23) | Regimen D (N = 23) |
|---|---|---|---|---|---|
| $C_{max}$ | ng/mL | 294 (384, 78) | 937 (1193, 84) | 633 (723, 54) | 803 (973, 72) |
| $T_{max}^a$ | h | 3.0 (1.5 to 5.0) | 4.0 (3.0 to 5.0) | 5.0 (4.0 to 6.0) | 2.0 (1.0 to 3.0) |
| $T_{1/2}^b$ | h | 6.0 (24) | 6.0 (16) | 6.3 (18) | 5.7 (16) |
| $AUC_t$ | ng · h/mL | 1150 (1430, 70) | 3040 (3460, 60) | 2110 (2390, 54) | 2620 (2970, 53) |
| $AUC_{inf}$ | ng · h/mL | 1150 (1440, 69) | 3040 (3470, 60) | 2120 (2390, 54) | 2620 (2980, 53) |

$^a$Median (Minimum to Maximum)
$^b$Harmonic mean (pseudo % CV)

TABLE 5b

Compound 2 Pharmacokinetic Parameters ((Geometric Mean (Mean, CV %))

| Pharmacokinetic Parameters | Units | Regimen A (N = 23) | Regimen B (N = 23) | Regimen C (N = 23) | Regimen D (N = 23) |
|---|---|---|---|---|---|
| $C_{max}$ | ng/mL | 116 (140, 60) | 221 (239, 44) | 237 (262, 45) | 175 (192, 38) |
| $T_{max}^a$ | h | 4.0 (2.0 to 5.0) | 5.0 (3.0 to 5.0) | 5.0 (4.0 to 6.0) | 4.0 (2.0 to 5.0) |
| $t_{1/2}^b$ | h | 13.3 (9) | 13.0 (10) | 13.5 (9) | 12.5 (8) |
| $AUC_t$ | ng · h/mL | 910 (1100, 64) | 1280 (1400, 49) | 1390 (1560, 49) | 1420 (1570, 40) |
| $AUC_{inf}$ | ng · h/mL | 960 (1160, 64) | 1350 (1480, 49) | 1460 (1650, 50) | 1490 (1650, 40) |

$^a$Median (Minimum to Maximum)
$^b$Harmonic mean (pseudo % CV)

The above studies showed that administration with food significantly improved the bioavailability of both Compound 1 and Compound 2, and the improvement was achieved with regard to the fat content in the food. Additional studies comparing film-coated to uncoated bilayer tablets further showed that film-coating had minimal impact on the bioavailability of co-formulated Compound 1 and Compound 2.

Example 4. Bioavailability of Compound 1/Compound 2 Mini-Tablets 14 subjects were enrolled in this study and dosed with co-formulated Compound 1/Compound 2 in mini-tablets. The study design is summarized in Tables 6a and 6b. One subject spilled 4 mini-tablets (out of 100-150 total mini-tablets) during dosing of Period 2 (Regimen G) and was not excluded from the analysis. The mini-tablets were prepared according to a process similar to that described in Example 2.

TABLE 6a

Single Dose, Crossover Clinical Study Design

| Sequence Number | Number of Subjects | Regimens | | |
|---|---|---|---|---|
| | | Period 1 | Period 2 | Period 3 |
| VII | 5 | F | G | J |
| VIII | 5 | G | J | F |
| IX | 5 | J | F | G |

TABLE 6b

Single Dose, Crossover Clinical Study Design

| Regimen F | Single dose of Compound 1/Compound 2 mini-tablets given under fasting conditions (total dose of 200 mg/120 mg Compound 1/Compound 2) |
|---|---|
| Regimen G | Single dose of Compound 1/Compound 2 mini-tablets given under non-fasting conditions (total dose of 200 mg/120 mg Compound 1/Compound 2) |
| Regimen J | Single dose of two Compound 1 tablets (each containing 100 mg Compound 1) and three Compound 2 tablets (each containing 40 mg Compound 2) under fasting conditions |

Table 7a shows the pharmacokinetic profiles of Compound 1 in these studies, as well as the food effect on the bioavailability of Compound 1. Table 7b shows the pharmacokinetic profiles of Compound 2, as well as the food effect on the bioavailability of Compound 2.

TABLE 7a

Compound 1 Pharmacokinetic Parameters ((Geometric Mean (Mean, CV %))

| Pharmacokinetic Parameters | Units | Regimen F (N = 14) | Regimen G (N = 14) | Regimen J (N = 14) |
|---|---|---|---|---|
| $C_{max}$ | ng/mL | 123 (164, 103) | 166 (314, 209) | 212 (333, 159) |
| $T_{max}$[a] | h | 1.0 (0.5 to 4.0) | 1.75 (1.0 to 4.0) | 1.5 (0.5 to 3.0) |
| $t_{1/2}$[b] | h | 5.61 (29) | 6.42 (31) | 5.93 (39) |
| $AUC_t$ | ng · h/mL | 428 (598, 107) | 699 (1020, 150) | 738 (1150, 165) |
| $AUC_{inf}$ | ng · h/mL | 432 (602, 107) | 704 (1020, 149) | 742 (1160, 164) |

[a]Median (Minimum to Maximum)
[b]Harmonic mean (pseudo % CV)

TABLE 7b

Compound 2 Pharmacokinetic Parameters ((Geometric Mean (Mean, CV %))

| Pharmacokinetic Parameters | Units | Regimen F (N = 14) | Regimen G (N = 14) | Regimen J (N = 14) |
|---|---|---|---|---|
| $C_{max}$ | ng/mL | 96.0 (110, 61) | 177 (198, 55) | 139 (169, 75) |
| $T_{max}$[a] | h | 4.0 (2.0 to 6.0) | 3.0 (3.0 to 5.0) | 4.5 (1.5 to 6.0) |
| $t_{1/2}$[b] | h | 13.4 (15) | 13.2 (10) | 13.3 (7) |
| $AUC_t$ | ng · h/mL | 863 (1050, 80) | 1250 (1480, 70) | 1190 (1570, 91) |
| $AUC_{inf}$ | ng · h/mL | 913 (1110, 80) | 1320 (1560, 71) | 1260 (1660, 92) |

[a]Median (Minimum to Maximum)
[b]Harmonic mean (pseudo % CV)

The above studies showed that administration with food significantly increased the bioavailability of both Compound 1 and Compound 2 when delivered in co-formulated mini-tablets.

The foregoing description of the present invention provides illustration and description, but is not intended to be exhaustive or to limit the invention to the precise one disclosed. Modifications and variations are possible in light of the above teachings or may be acquired from practice of the invention. Thus, it is noted that the scope of the invention is defined by the claims and their equivalents.

The invention claimed is:

1. A solid oral pharmaceutical tablet comprising:
a first composition comprising:
50% to 80% by weight of one or more pharmaceutically acceptable polymers, and 100 mg Compound 1

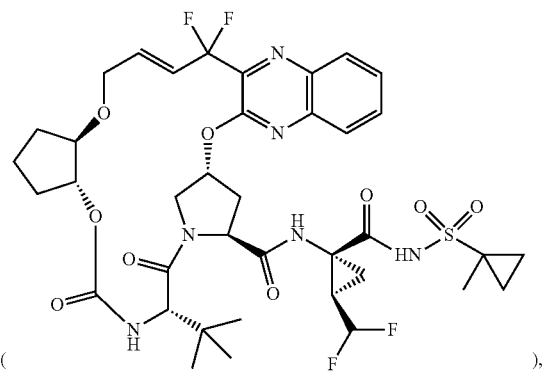 [SMILES: CC(C)(C)[C@@H]1NC(=O)O[C@@H]2CCC[C@H]2OC/C=C/C(F)(F)c2nc3ccccc3nc2O[C@@H]2C[C@@H](C(=O)N[C@]3(C(=O)NS(=O)(=O)C4(C)CC4)C[C@H]3C(F)F)N(C2)C1=O]

wherein the weight percentage of the one or more pharmaceutically acceptable polymers is relative to the total weight of the first composition; and
a second composition comprising:
50% to 90% by weight of one or more pharmaceutically acceptable polymers, and 40 mg Compound 2

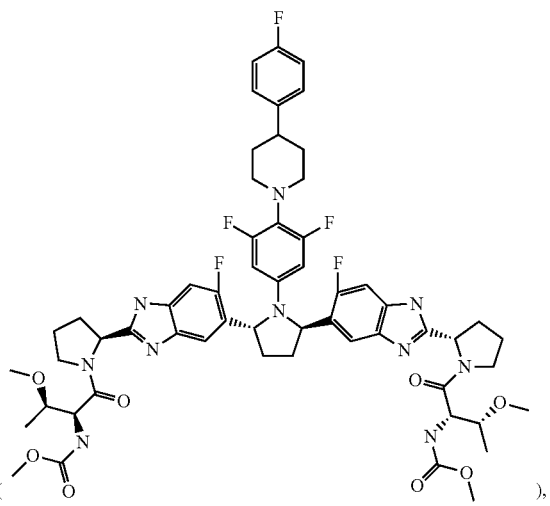

wherein the weight percentage of the one or more pharmaceutically acceptable polymers is relative to the total weight of the second composition;
wherein the tablet comprises a first layer and a second layer, the first layer comprising the first composition and the second layer comprising the second composition; and
wherein administration of a single dose comprising three of the tablets delivered at the same time to each individual in a population of healthy, non-fasted adult humans results in a mean Cmax value between about 333 ng/mL and about 1113 ng/mL for Compound 1.

2. The pharmaceutical tablet of claim 1,
wherein the first composition comprises a first amorphous solid dispersion comprising Compound 1.

3. The pharmaceutical tablet of claim 1,
wherein the second composition comprises a second amorphous solid dispersion comprising Compound 2.

4. The pharmaceutical tablet of claim 2,
wherein the first amorphous solid dispersion comprises the one or more pharmaceutically acceptable polymers.

5. The pharmaceutical tablet of claim 2,
wherein the first amorphous solid dispersion further comprises one or more pharmaceutically acceptable surfactants.

6. The pharmaceutical tablet of claim 4,
wherein the first amorphous solid dispersion further comprises one or more pharmaceutically acceptable surfactants.

7. The pharmaceutical tablet of claim 3,
wherein the second amorphous solid dispersion comprises the one or more pharmaceutically acceptable polymers.

8. The pharmaceutical tablet of claim 3,
wherein the second amorphous solid dispersion further comprises one or more pharmaceutically acceptable surfactants.

9. The pharmaceutical tablet of claim 7,
wherein the second amorphous solid dispersion further comprises one or more pharmaceutically acceptable surfactants.

10. The pharmaceutical tablet of claim 6,
wherein the one or more pharmaceutically acceptable polymers comprise copovidone, and the one or more pharmaceutically acceptable surfactants comprise Vitamin E TPGS.

11. The pharmaceutical tablet of claim 9,
wherein the one or more pharmaceutically acceptable polymers comprise copovidone, and the one or more pharmaceutically acceptable surfactant comprises Vitamin E TPGS.

12. The pharmaceutical tablet of claim 11,
wherein the one or more pharmaceutically acceptable surfactants further comprise propylene glycol monocaprylate.

13. The pharmaceutical tablet of claim 1,
wherein
the first composition comprises a first amorphous solid dispersion comprising Compound 1, one or more pharmaceutically acceptable polymers and one or more pharmaceutically acceptable surfactants; and
the second composition comprises a second amorphous solid dispersion comprising Compound 2, one or more pharmaceutically acceptable polymers and one or more pharmaceutically acceptable surfactants.

14. The pharmaceutical tablet of claim 13,
wherein the one or more pharmaceutically acceptable polymers comprise copovidone, and
the one or more pharmaceutically acceptable surfactants comprises Vitamin E TPGS.

15. The pharmaceutical tablet of claim 3, wherein the first amorphous solid dispersion comprises Compound 1, one or more pharmaceutically acceptable polymers comprising copovidone, and one or more pharmaceutically acceptable surfactants comprises Vitamin E TPGS; and the second amorphous solid dispersion comprises Compound 2, one or more pharmaceutically acceptable polymers comprising copovidone, and one or more pharmaceutically acceptable surfactants comprising Vitamin E TPGS and Propylene glycol monocaprylate.

16. The pharmaceutical tablet of claim 1, wherein the first amorphous solid dispersion comprises 10% to 40% by weight of Compound 1, and the second amorphous solid dispersion comprises 5% to 20% by weight of Compound 2.

17. The pharmaceutical tablet of claim 1, wherein the first amorphous solid dispersion comprises 15% to 30% by weight of Compound 1, and the second amorphous solid dispersion comprises 5% to 15% by weight of Compound 2.

18. The pharmaceutical tablet of claim 13, wherein the first amorphous solid dispersion comprises 15% to 30% by weight of Compound 1, and the second amorphous solid dispersion comprises 5% to 15% by weight of Compound 2.

19. The pharmaceutical tablet of claim 15, wherein the first amorphous solid dispersion comprises 15% to 30% by weight of Compound 1, and the second amorphous solid dispersion comprises 5% to 15% by weight of Compound 2.

20. The pharmaceutical tablet of claim 1, wherein the first layer further comprises a disintegrant.

21. The pharmaceutical tablet of claim 20, wherein the disintegrant comprises Croscarmellose sodium.

22. The pharmaceutical tablet of claim 1, wherein the first layer and the second layer further comprise a lubricant.

23. The pharmaceutical tablet of claim 22, wherein the lubricant comprises sodium stearyl fumarate.

24. A solid oral pharmaceutical tablet comprising: a first composition comprising:
50% to 80% by weight of one or more pharmaceutically acceptable polymers, and 100 mg Compound 1

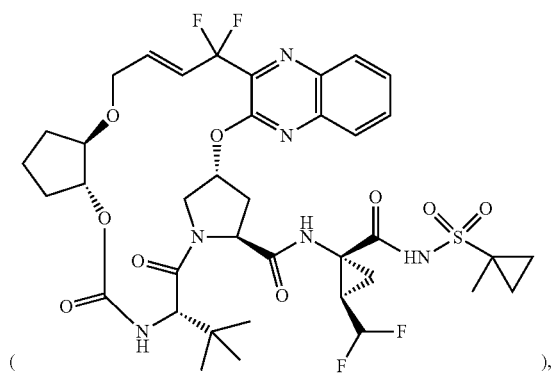

wherein the weight percentage of the one or more pharmaceutically acceptable polymers is relative to the total weight of the first composition; and a second composition comprising:
50% to 90% by weight of one or more pharmaceutically acceptable polymers, and 40 mg Compound 2

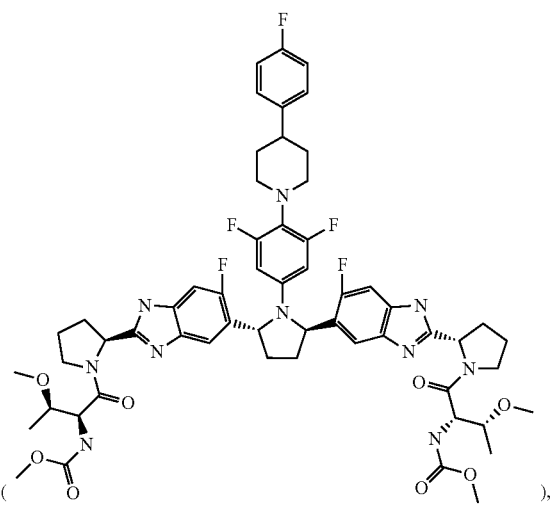

wherein the weight percentage of the one or more pharmaceutically acceptable polymers is relative to the total weight of the second composition;

wherein the tablet comprises a first layer and a second layer, the first layer comprising the first composition and the second layer comprising the second composition; and wherein administration of a single dose comprising three of the tablets delivered at the same time to each individual in a population of healthy, non-fasted adult humans results in a mean AUC value between about 1099 ng·h/mL and about 3680 ng·h/mL for Compound 1.

25. A solid oral pharmaceutical tablet comprising:

a first composition comprising:
50% to 80% by weight of one or more pharmaceutically acceptable polymers, and 100 mg Compound 1

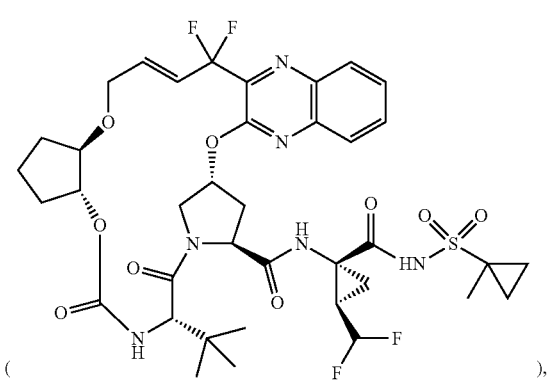 [SMILES: CC(C)(C)[C@@H]1NC(=O)O[C@@H]2CCC[C@H]2OC/C=C/C(F)(F)c2nc3ccccc3nc2O[C@@H]2C[C@@H](C(=O)N[C@]3(C(=O)NS(=O)(=O)C4(C)CC4)C[C@H]3C(F)F)N(C2)C1=O]

wherein the weight percentage of the one or more pharmaceutically acceptable polymers is relative to the total weight of the first composition; and a second composition comprising:
50% to 90% by weight of one or more pharmaceutically acceptable polymers, and 40 mg Compound 2

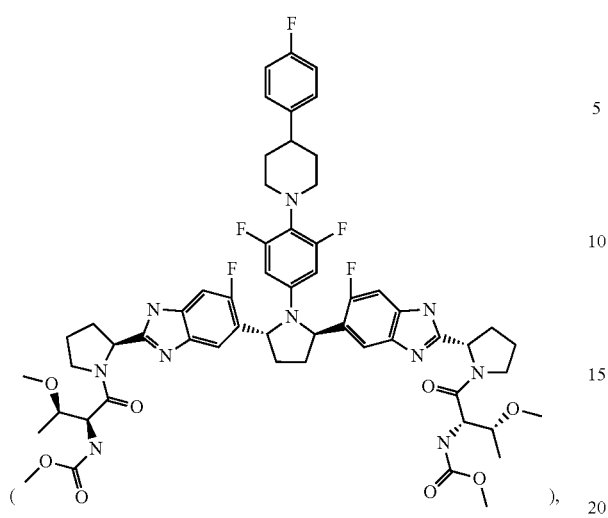

), wherein the weight percentage of the one or more pharmaceutically acceptable polymers is relative to the total weight of the second composition;
wherein the tablet comprises a first layer and a second layer, the first layer comprising the first composition and the second layer comprising the second composition; and
wherein administration of a single dose comprising three of the tablets delivered at the same time to each individual in a population of healthy, fasted adult humans results in a mean $C_{max}$ value between about 85 ng/mL and about 684 ng/mL for Compound 1.

26. A solid oral pharmaceutical tablet comprising:
a first composition comprising:
50% to 80% by weight of one or more pharmaceutically acceptable polymers, and 100 mg Compound 1

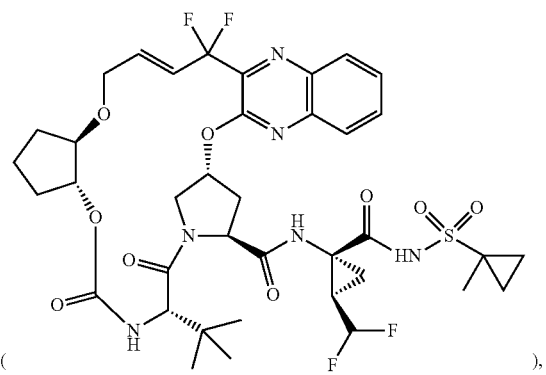 [SMILES: CC(C)(C)[C@@H]1NC(=O)O[C@@H]2CCC[C@H]2OC/C=C/C(F)(F)c2nc3ccccc3nc2O[C@@H]2C[C@@H](C(=O)N[C@]3(C(=O)NS(=O)(=O)C4(C)CC4)C[C@H]3C(F)F)N(C2)C1=O]

), wherein the weight percentage of the one or more pharmaceutically acceptable polymers is relative to the total weight of the first composition; and a second composition comprising:
50% to 90% by weight of one or more pharmaceutically acceptable polymers, and 40 mg Compound 2

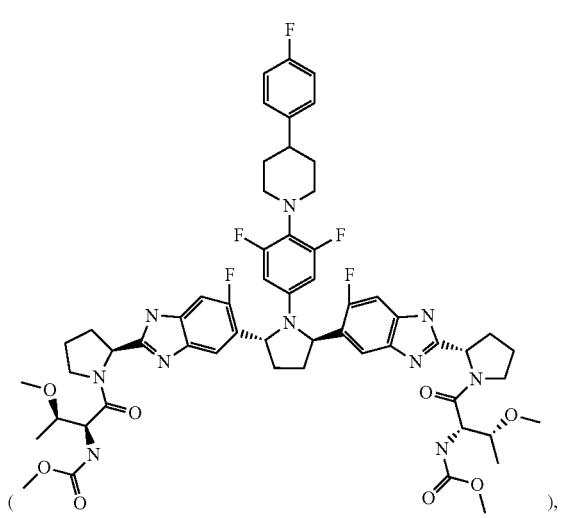

), wherein the weight percentage of the one or more pharmaceutically acceptable polymers is relative to the total weight of the second composition;
wherein the tablet comprises a first layer and a second layer, the first layer comprising the first composition and the second layer comprising the second composition; and
wherein administration of a single dose comprising three of the tablets delivered at the same time to each individual in a population of healthy, fasted adult humans results in a mean AUC value between about 429 ng·h/mL and about 2431 ng·h/mL for Compound 1.

27. A solid oral pharmaceutical tablet that is bioequivalent to a solid oral pharmaceutical tablet comprising:
a. 500 mg of Compound 1 20% extrusion granulation, comprising:
   i. 20% (100 mg) Compound 1,
   ii. 69% copovidone,
   iii. 10% vitamin E TPGS, and
   iv. 1% colloidal silicon dioxide;
b. 400 mg of Compound 2 10% extrusion granulation, comprising
   i. 10% (40 mg) Compound 2,
   ii. 79% copovidone,
   iii. 8% vitamin E TPGS,
   iv. 2% propylene glycol monocaprylate, and
   v. 1% colloidal silicone dioxide;
c. 26.3 mg croscarmellose sodium;
d. 4.7 mg colloidal silicon dioxide;
e. 4.7 mg sodium stearyl fumarate; and
f. 28.1 mg HPMC coating.

* * * * *